United States Patent [19]
Kosaka et al.

[11] Patent Number: 5,506,673
[45] Date of Patent: Apr. 9, 1996

[54] PARTICLE ANALYZER

[75] Inventors: Tokihiro Kosaka, Kakogawa; Kaoru Takarada, Miki, both of Japan

[73] Assignee: Toa Medical Electronics Co., Ltd., Hyogo, Japan

[21] Appl. No.: 332,040

[22] Filed: Nov. 1, 1994

[30] Foreign Application Priority Data

Nov. 4, 1993 [JP] Japan .................................. 5-275422

[51] Int. Cl.$^6$ .......................... G01N 15/12; G01N 15/14
[52] U.S. Cl. .............................................. 356/72; 356/336
[58] Field of Search ................................. 356/72, 73, 336

[56] References Cited

U.S. PATENT DOCUMENTS

| | | |
|---|---|---|
| 3,887,868 | 6/1975 | Guggenbuhl . |
| 4,298,836 | 11/1981 | Groves et al. . |
| 5,257,087 | 10/1993 | Furuya .................................. 356/336 |

FOREIGN PATENT DOCUMENTS

| | | |
|---|---|---|
| 60-128327 | 7/1985 | Japan . |
| 2-25133 | 5/1990 | Japan . |
| 3194444A | 8/1991 | Japan . |
| 3-194444 | 8/1991 | Japan . |

*Primary Examiner*—Vincent P. McGraw

[57] ABSTRACT

A particle analyzer includes a flow cell for enclosing an electrolyte flow containing particles in a sheathed flow, the flow cell including a first and second cells which are interconnected through an orifice, the sheathed flow flowing through the orifice from the first cell to the second cell, a first and second electrodes provided in the first and second cells, respectively and a voltage application device for applying voltage between the first and second electrodes. The particle analyzer further includes a resistance detection device for detecting a variation of electric resistance between the first and second electrodes when the particle passes through the orifice to output the detected variation as a resistance detection signal. A first diameter calculation device is included for calculating each diameter of the particles based on the detected variation of electric resistance. Further a light source device for emitting a light beam to the particles enclosed in the sheathed flow and a light detection device for detecting each intensity of scatter light of the particles irradiated with the light beam to output the detected intensity as a scatter light detection signal are included. Finally, the particle analyzer includes a refractive index calculation device for calculating a refractive index of the particle based on the resistance detection signal and the scatter light detection signal and a second diameter calculation device for calculating each diameter of the particles based on the calculated refractive index and the scatter light detection signal.

7 Claims, 7 Drawing Sheets

PARTICLE ANALYZER

BACKGROUND OF THE INVENTION

1. Field of the Invention

The present invention relates to a particle analyzer, and more particularly to a particle analyzer for analyzing morphology of particles such as a fine ceramic powder, pigment powder or cosmetic powder.

2. Description of the Related Art

It is extremely important to measure and analyze the size of particles for controlling the quality of a powder such as a fine ceramic powder, pigment powder, cosmetic powder or the like. A conventionally available measuring device uses a liquid sedimentation method or an electrozone method (Coulter principle) whereas a currently known measuring device uses a laser diffraction method.

However, none of measuring devices using the aforementioned methods are satisfactory in terms of precision (accuracy) in measurement and measuring range thereof. In particular, when a particle to be measured has a flat or elongated shape, the particle diameter to be measured will be largely different depending on the measuring method. Besides, even when the same measuring method is adopted, measured values are largely different and peculiar particle size distribution curves are given depending on the type of the measuring device.

Since larger particles sediment faster than smaller particles in a suspension, the concentration of particles varies with the lapse of time and in three demensions. A method for determining a particle size distribution by detecting the particle concentration based on an amount of light transmitted though the suspension is a liquid sedimentation light transmitting method, which is typical as the liquid sedimentation method. A device using this method has the following drawbacks:

(i) when the particle has a diameter on the submicron order or less, the measured particle size must be corrected by a light absorption constant corresponding to the refractive index and particle diameter thereof, (ii) the brownian motion and convection of the particles affect the measurement of the particle size, (iii) it takes a considerable time to measure the particle size, and (iv) reproducibility of the measured data and integrity between different types of devices are not so favorable.

A device using the electrozone method detects a variation in electric resistance that appears when particles floating in an electrolyte pass through an orifice. The device has the advantage that the volume-equivalent diameter of the particle can be measured with virtually no influence from the shape thereof. However, the device using the method has also the following drawbacks:

1) The range in which the diameter of particles can be measured with one kind of orifice is very narrow, since the particles that are smaller than the orifice remain undetected and since the particles that are larger than the orifice clog the orifice.

2) Since no accurate particle volume can be measured when the particles do not pass through the center of the orifice, no reliable particle size distribution can be obtained.

3) When the detection region is wide, the probability is high that two or more particles pass through the orifice at the same time. In this case, the method fails to provide an accurate particle volume and a reliable size particle distribution.

4) The electrozone method can measure a particle having a diameter larger than about 0.5 μm. It is very difficult for the method to measure a small particle having a diameter less than 0.5 μm.

A device using the currently available laser diffraction method calculates a particle size distribution based on the Mie's Scattering Theory from information on the angle distribution of the intensity of diffraction light and scatter light obtained by irradiating a suspended group of particles with a laser beam. This type of device has the advantage that only one time measurement provides reproducible data of particle size distribution with respect to particles having a diameter of 1 μm to several hundred μm. However, this type of device has the following drawbacks:

1) A difference in shape, refractive index, and surface state or the like largely affects an intensity of light scattered by particles, and it is very difficult, in particular, to determine an accurate particle size distribution with respect to particles having a size of submicron order.

2) This type of device requires a real refractive index of particle to be measured. An accurate particle size distribution cannot be obtained owing to oxidation of the particle surface and contamination of the particle when the refractive index given to the device is a normal value.

3) A particle size distribution is calculated on the assumption that the particle has a round shape and smooth surface but cannot be calculated when the assumption cannot be established.

4) The measurement results may be largely different between different types of devices because they differ in mitigation for the above drawbacks.

Furthermore, particle analyzers are known which primarily analyze a blood cell or a cell with a combination of the electrozone method and the laser diffraction method (for example, refer to Japanese Published Examined Patent Application No. HEI 2-25133, Japanese Published Unexamined Patent Application No. HEI 3-194444, and Japanese Published Examined Patent Application No. HEI 4-49903).

However, these combination type particle analyzers for analyzing only blood cells or cells analyze particles having a diameter large enough to be detected by both the electrozone method and the laser diffraction method in order to increase the amount of analysis information. They are not intended to measure sizes of much finer particles.

The electrozone method allows such analyzer to detect the particle having a diameter larger than about 0.5 μm whereas the laser diffraction method allows such particle analyzer to detect the particle having a diameter larger than about 0.1 μm.

SUMMARY OF THE INVENTION

The present invention has been made in view of the aforementioned points, and the object of the invention is to provide a particle analyzer that combines the electrozone method with the laser diffraction method to detect fine particles having a diameter that cannot be detected with the conventional electrozone method.

The present invention provides a particle analyzer comprising: a flow cell for enclosing an electrolyte flow containing particles in a sheathed flow, the flow cell including a first and second cells which are interconnected through an orifice, the sheathed flow flowing through the orifice from the first cell to the second cell; a first and second electrodes provided in the first and second cells, respectively; voltage application means for applying voltage between the first and second electrodes; resistance detection means for detecting a variation of electric resistance between the first and second electrodes when the particle passes through the orifice to output the detected variation as a resistance detection signal; first diameter calculation means for calculating each diameter of the particles based on the detected variation of electric resistance; light source means for emitting a light beam to the particles enclosed in the sheathed flow; light detection means for detecting each intensity of scatter light of the particles irradiated with the light beam to output the detected intensity as a scatter light detection signal; refractive index calculation means for calculating a refractive index of the particle based on the resistance detection signal and the scatter light detection signal; and second diameter calculation means for calculating each diameter of the particles based on the calculated refractive index and the scatter light detection signal.

BRIEF DESCRIPTION OF THE DRAWINGS

The present invention will be detailed in conjunction with the accompanying drawings, but the invention is not limited thereto.

DESCRIPTION OF THE PREFERRED EMBODIMENTS

Examples of particles to be analyzed by the particle analyzer of the present invention includes powder such as fine ceramic powder, pigment powder, cosmetic powder or the like. A conventionally known flow cell can be used as the flow cell of the present invention.

Preferably, a constant current power source can be used as the voltage application means. This means that a variation in electric resistance between the electrodes can be detected as a variation in voltage between the electrodes.

Preferably, a laser beam light source is used as the light source means of the present invention. In addition, the light source means preferably irradiates the orifice of the flow cell, an outlet of the orifice or an inlet thereof so that an output of the resistance detection means and an output of the light detection means are facilitated.

A photodiode, a phototransistor, a photomultiplier or the like can be used as the light detection means.

The variation of electric resistance as seen in the conventional electrozone method, assumes a chevron-like pulse waveform when the particle passes through the orifice. It is already known that the height of the pulse is approximately proportional to the volume of the particle when the particle has a diameter of about 2 to 50% of the diameter of the orifice.

Consequently, the resistance detection means determines a volume-equivalent diameter and the light detection means determines an intensity of scatter light with respect to the particles having a diameter of about 2% or more of the diameter of the orifice.

Then, the refractive index calculation means calculates a refractive index of the particle by using the relation among the particle diameter, the intensity of scatter light and the refractive index based on the Mie's Scattering Theory.

On the other hand, since the light detection means detects the scatter light intensity with respect to the particles having a diameter of about 2% or less of the diameter of the orifice, the second diameter calculation means calculates the particle diameter (scatter light intensity-equivalent diameter) from the refractive index and the intensity of scatter light based on the Mie's Scattering Theory. In this manner, the analyzer of the present invention can measure not only the particles having a diameter of 2% or more of the diameter of the orifice but also the particles having a diameter of 2% or less of the diameter of the orifice.

Preferably, the refractive index calculation means and the first and second diameter calculation means comprise a microcomputer including a CPU, a ROM, and a RAM. Desirably, an appropriate display such as a cathode ray tube (CRT) or a liquid crystal display displays the result of the calculation performed by each calculation means.

The particle analyzer may further comprise measuring means for measuring intervals between the scatter light detection signals obtained when a plurality of particles serially flow in the sheath flow; and particle size distribution calculation means for calculating a particle size distribution based on the calculated diameters of the particles, except the particles of which scatter light detection signals have intervals shorter than a predetermined time.

The particle analyzer may further comprise calculation means for calculating a mean value or a cumulative value of the intervals measured with respect to a predetermined number of particles to monitor a clogging state of the orifice or a stability of the sheathed flow.

The light detection means may comprise first light detection means for detecting an intensity of forward scatter light of the particle to output the detected intensity as a forward scatter light detection signal; second light detection means for detecting an intensity of side scatter light of the particle to output the detected intensity as a side scatter light detection signal; and adding means for adding the forward scatter light detection signal to the side scatter light detection signal to output the added signals as the scatter light detection signal.

The particle analyzer may further comprise index calculation means for calculating an index of roundness or agglutination rate of the particle from a deviation of the intensity of side scatter light obtained with respect to a plurality of particles which are the same in magnitude of the resistance detection signal. The particle analyzer may further comprise ratio calculation means for calculating a ratio of the forward or side scatter light intensity to the scatter light intensity, and index calculation means for calculating an index of roundness or agglutination rate of the particle from a deviation of the ratio calculated with respect to a plurality of particles which are the same in magnitude of the resistance detection signal.

The particle analyzer may further include ratio calculation means for calculating a ratio of the forward or side scatter light intensity to the scatter light intensity with respect to a plurality of particles having a nearly spherical shape and a known refractive index, and an index calculating means for calculating an index of surface smoothness, surface optical characteristics, or agglutination rate of the particle.

The present invention will be detailed in conjunction with embodiments shown in the accompanying drawings, but they are not intended to limit the scope of the present invention.

Figure 1:
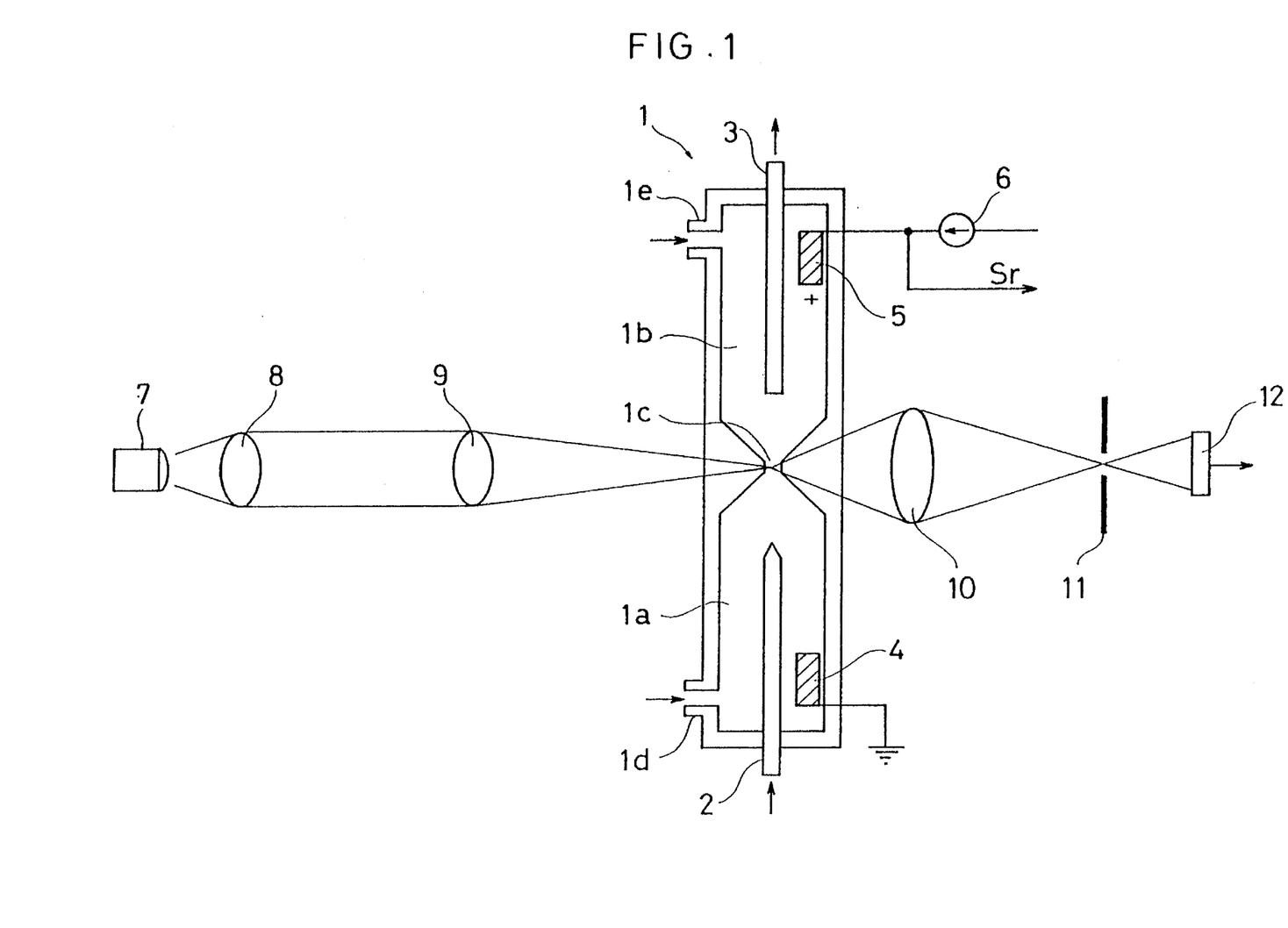
FIG. 1 is a side view showing a structure of an embodiment according to the present invention.
Figure 2:
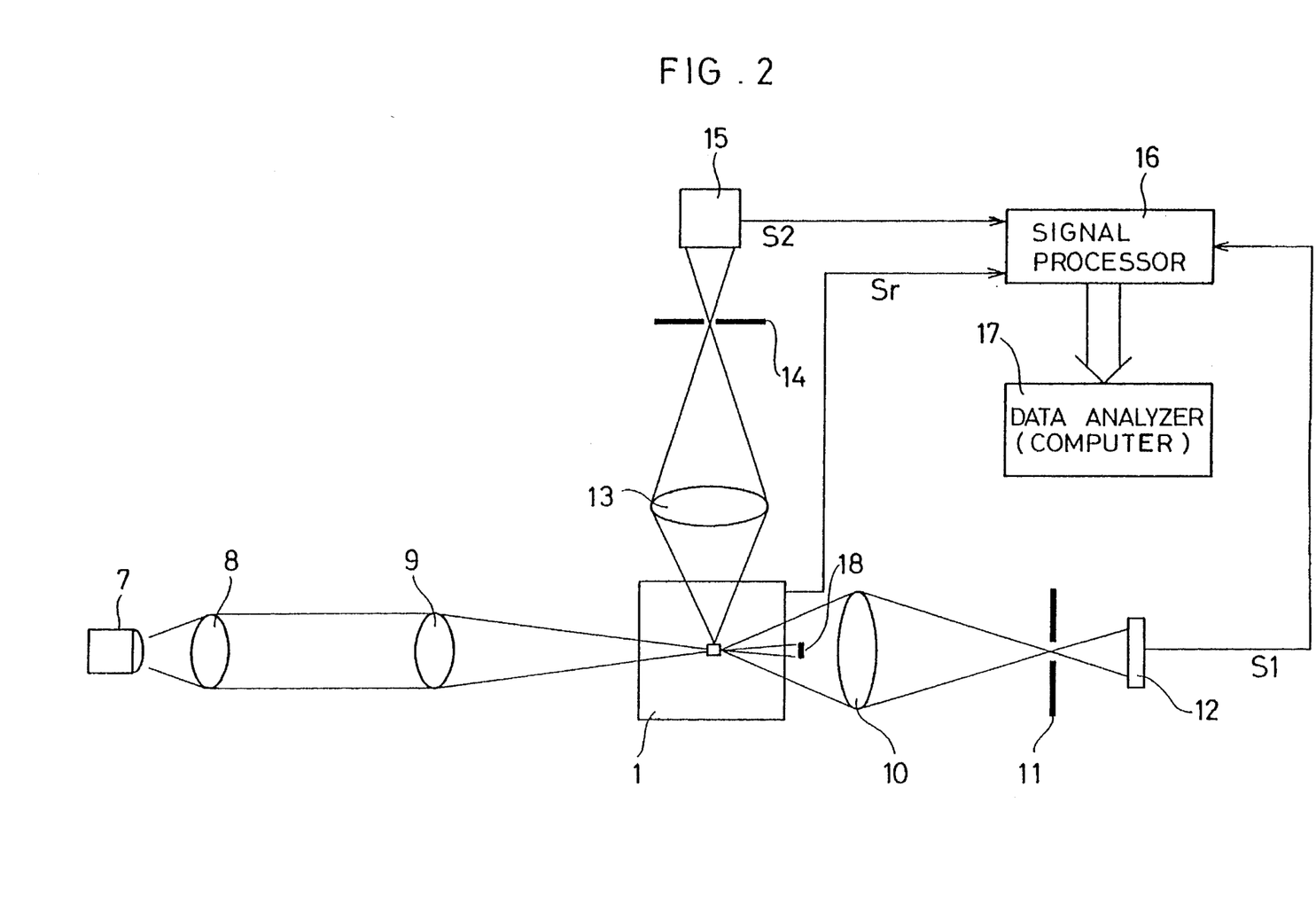
FIG. 2 is a top view showing the structure of the embodiment according to the present invention.

FIG. 1 is a side view showing a structure of an embodiment of the present invention. FIG. 2 is a top view thereof. Referring to FIGS. 1 and 2 show a flow cell 1, a first cell 1a, a second cell 1b, an orifice portion 1c having an orifice to connect the first cell 1a to the second cell 1b, a supply port 1d for supplying an electrolyte as a front sheath liquid to the first cell 1a, a supply port 1e for supplying an electrolyte as a back sheath liquid to the second cell 1b, a sample nozzle 2 for injecting a sample liquid (electrolyte) containing particles To the first cell 1a, and a recycling pipe 3 for discharging the sample liquid from the second cell 1b.

In addition, FIGS. 1 and 2 show a cathode electrode 4 set inside of the first cell 1a, an anode electrode 5 set inside of the second cell 1 b, a constant current power source 6 for applying voltage between electrodes 4 and 5, a laser beam light source 7, a collimator lens 8, a condenser lens 9, a collector lens 10, a pin hole type iris 11, a photodetector (photodiode) 12, a collector lens 13, a pin hole type iris 14, a photodetector (photomultiplier) 15, a signal processor 16, and a data analyzer (computer) 17.

As shown in FIG. 1, the flow cell 1 has a structure for combining the electrozone method and the laser diffraction method. The orifice portion 1c for grasping a variation in electric resistance is irradiated with a laser beam. When a particle passes through the orifice portion 1c, the variation in the electric resistance and an intensity of scatter light of the particle can be detected at the same time. The sample liquid which contains the particles is ejected from the sample nozzle 2 to the first cell 1. A sample liquid is focused to a thin flow by surrounding with front sheath liquid. The focused sample flow passes through the center of the orifice portion 1c in the center of the flow cell 1. A certain amount of electric current flows through the orifice portion 1c from the electrode 5 to the electrode 4. The passage of the particle through the orifice portion 1c changes the flow degree of the electric current or the electric resistance between electrodes. The quantity of electric resistance reflects the volume of particle which passes through the orifice portion 1c with the result that the volume-equivalent diameter can be determined without any influence from the shape of the particle.

As shown in FIG. 2, the collimator lens 8 collimates a beam coming from the laser light source 7, and then the condenser lens 10 focuses the collimated beam so that the orifice portion 1c is irradiated with the focused beam. When the laser beam is given as a Gaussian beam, the intensity of the Gaussian beam is preferably uniformed. The Gaussian beam refers to a beam whose irradiation intensity distribution assumes a Gaussian distribution. As a method for uniforming the Gaussian beam, a method using two combined non-spherical lenses are known. These lenses are preferably inserted between the collimator lens 8 and the condenser lens 9.

A beam stopper 18 cuts direct light coming from the laser beam light source 7 whereas the collector lens 10 collects forward scatter light of the particle, which will be incident on the photodetector 12 (photodiode) via the iris 11. The iris (pin hole) 11 detects only the scatter light coming from a region where particles are irradiated. The S/N ratio of a detection signal of the photodetector 12 is secured by dispensing with the detection of stray light generated inside of the wall of the orifice portion 1c. The collector lens 13 collects side scatter light of the particle, which light will be incident on the the photodetector (photomultiplier) 15 via the iris 14. Forward and side scatter light detection signals S1 and S2 detected by The photodetectors 12 and 15 and an electric resistance detection signal Sr are input into the signal processor 16. The signal processor 16 processes each kind of signal to determine information on a volume-equivalent diameter of each particle, an intensity of the scatter light or the like.

By the way, an intensity of scatter light obtained by using a single wavelength laser beam does not monotonously increase with respect to the particle diameter. An intensity of forward scatter light oscillates to increase when the particle diameter assumes about 3 μm or more, while an intensity of side scatter light slightly oscillates to increase when the particle diameter assumes about 0.3 μm or more. However, addition of the intensity of the forward scatter light to the intensity of the side scatter light at a certain ratio allows the the relation between the particle diameter and the scatter light intensity to come considerably close to a monotonous increase relation. In addition, most of the particles that can be actually measured assume no complete spherical shape. Compared with an error in the particle measurement error due to the deviation in the morphology of particles, the error in the particle diameter measurement owing to the small oscillation of the above relation can be virtually ignored.

The present invention intends to suppress the above oscillation as much as possible by rendering as small as possible the light collecting angle of the forward scatter light and rendering as large as possible the light collecting angle of the side scatter light. Furthermore, the photodiode 12 receives the forward scatter light whereas the photo multiplier 15 having a light intensification function receives the side scatter light. The detection signals output from the two photodetectors 12 and 15 having different detection sensitivities are added. The magnitude of the added signals is A/D converted as an intensity of the scatter light. Several kinds of standard round particles are to be preliminarily measured which have been made clear as to the particle diameter and the refractive index. When the relation between the scatter light and the particle diameter is stored in the analyzer 17 as reference data, the diameter of an individual particle corresponding to the scatter light can be determined based on the intensity of scatter light and the refractive index. The particle diameter can be inferred in the following manner with respect to the small particles whose refractive index is indefinite and which cannot be measured with the electrozone method.

When the inner diameter of the orifice portion 1c is 100 μm in the flow cell 1 shown in FIG. 1, the measurement of the volume-equivalent diameter of the particle by the electrozone method ranges about 2 to 50 μm. The range of measurement of the particle diameter by the laser diffraction method changes by the output power of the laser light source, the wavelength of the laser beam, the diameter of the focused beam, the open angle of the collector lens, the dynamic range of the photodetectors and the signal processor. But the range of measurement is usually set about 0.2 to 10 μm. In this case the range in which both the volume-equivalent diameter and the intensity of scatter light can be measured is 2 to 10 μm.

In a device having such a measurement range, when sample powders are measured which have diameters deviating, for example, in the range of 0.5 to 5 μm, the volume-equivalent diameter of particles having a diameter of 0.5 to 2 μm cannot be determined by the electrozone method and only information on the intensity of scatter light can be obtained.

In such a case, when the refractive index of the particles is not clear, the particle diameter cannot be accurately determined from the intensity of scatter light. However, information on both the volume-equivalent diameter and the intensity of scatter light can be measured with respect to the particles having a diameter of 2 to 5 μm. The refractive index of particles can be inferred from an analysis based on the Mie's Scattering Theory by using the relation between the scatter light intensity and data on light collecting angle with respect to the scatter light. With respect to the particles having a diameter of 2 μm or less, the particle diameter can be calculated with the intensity of scatter light and the inferred refractive index.

Figure 5:
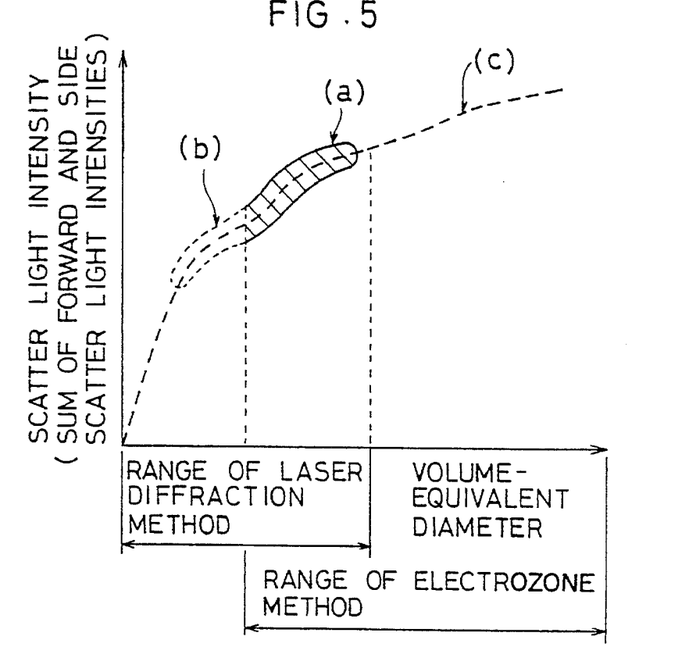
FIG. 5 is a characteristic view showing the relation between a volume-equivalent diameter and an intensity of scatter light.

FIG. 5 shows an example of the measurement result of the volume-equivalent diameter and the above scatter light intensity obtained by the electric electrozone method. A portion (a) shown by slanted lines in FIG. 5 designates a region where both volume-equivalent diameter and the scatter light intensity-equivalent volume can be measured whereas a portion (b) surrounded by a dashed line designates a region where only the intensity of scatter light can be measured. A curve (c) designates a theoretical curve calculated by using the inferred refractive index and the Mie's Scattering Theory assuming that the particles have a spherical shape and a smooth surface. When the volume-equivalent diameter of a group of particles exhibiting the same intensity of scatter light is not so deviated, the volume-equivalent diameter of the particles in the portion (b) can be determined by using the theoretical curve (c) from the intensity of scatter light.

When the maximum diameter of the particles to be measured is smaller than the lower limit of measurement using the electro-zone method, the volume-equivalent diameter and the intensity of scatter light cannot be obtained at the same time. In such a case, the refractive index of particles cannot be inferred as described above. When the refractive index of particles is unknown, no accurate diameter can be determined. However, even in such a case, when larger particles are available which are made of the same material as the particle to be measured, data on both the volume-equivalent diameter and the intensity of scatter light can be obtained so that the refractive index of the particle can be determined. When information on the refractive index is inferred, the diameter of small particles can be calculated from the intensity of the scatter light.

The present invention utilizes not only the intensity of scatter light obtained by adding the forward scatter light and the side scatter light, but also single intensity of side scatter light or forward scatter light, as well as the ratio of the intensity of side scatter light to the intensity of scatter light (rate of the side scatter light intensity) and the ratio of the foreward scatter light to the intensity of scatter light (rate of the forward scatter light intensity). Such data provides us with information on whether the particles have an approximately spherical shape or a smooth surface.

Figure 6:
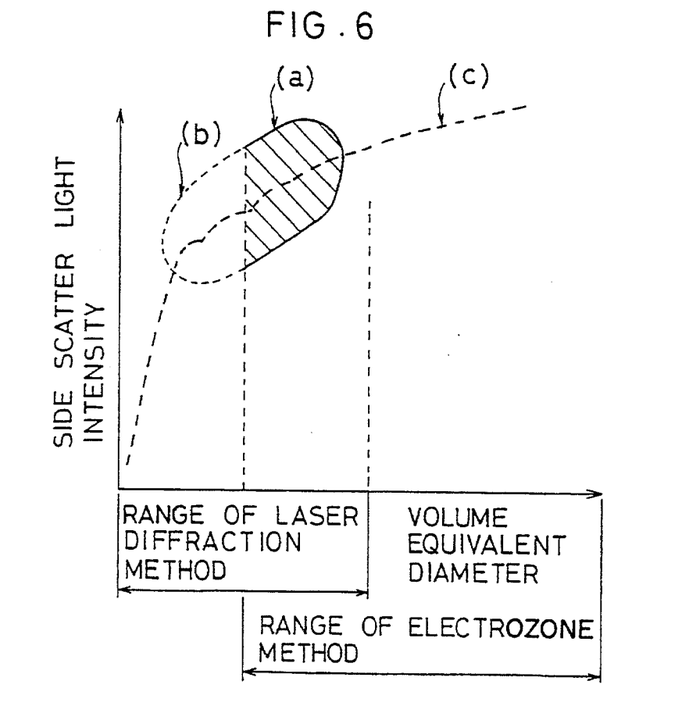
FIG. 6 is a characteristic view showing the relation between the volume-equivalent diameter and an intensity of side scatter light.

For example, assuming that the measurement result of the volume-equivalent diameter and the scatter light intensity is obtained as shown in FIG. 6, it is apparent that the intensity of side scatter light of the group of particles having the same volume-equivalent diameter deviates in a considerable range. Generally, as the shape of the particle deviates from a spherical shape, the intensity of side scatter light, or the ratio of the intensity of side scatter light to the intensity of scatter light deviates. An index of the roundness can be obtained by calculating the deviation.

For example, the index showing roundness can be determined by the equation as shown hereinbelow. That is, when the intensity of the j-th particle in a group of ni particles having a volume-equivalent diameter of Vi is designated by $SSij$, the mean value of the side scatter light of the group is designated by $SSi$, the distribution $Si^2$ of ni particles normalized by the mean value are determined from the following equation.

$$Si^2 = \sum_{j=1}^{ni} ((SSij - SSi)/SSi)^2$$

The distribution $S^2$ of n particles having a volume-equivalent diameter of Va to Vb is determined from the following equation.

$$S^2 = \sum_{i=a}^{b} Si^2$$

The ratio of deviation from the theoretical value of the number of particles N is determined by dividing the SN value by the total number of particles n. When the value obtained by adding 1 to the square root of the mean value of $S_2$ is set to be a surface properties index (R1), the following formula is obtained.

$$\text{Roundness Index } (RI) = (S^2/n)^{1/2} + 1$$

When the index is nearly equal to 1, the index indicates that the shape of the particle is approximately spherical or that the number of spherical particles are large.

The roundness index of the group of particles having a volume-equivalent diameter that cannot be measured is determined by the same method as described above from the deviation in the side scatter light intensity of the group of particles having approximately the same value of the scatter light intensity in which the forward scatter light intensity and the side scatter light intensity are added. However, small particles having a diameter on the submicron order tends to agglutinate to each other. In such a case, it is difficult to know whether the particles have a round shape or not.

When the small particles are measured which tend to agglutinate to each other, even particles having the same volume-equivalent diameter have largely deviated intensity of side scatter light. For example, when a secondary particle comprised of an aggultination of two round particles having a volume of V are compared with one round particle having a volume of 2 V, the volume-equivalent diameters thereof are the same, but the secondary particles have a larger rate of the side scatter light intensity. Consequently, the aforementioned roundness index is not reliable with respect to the particles which tend to agglutinate to each other. However, when it is known in advance that the particles to be measured have a round and smooth surface, the index determined from the aforementioned formula can be treated as one index showing the aggultination degree of particles.

Figure 7:
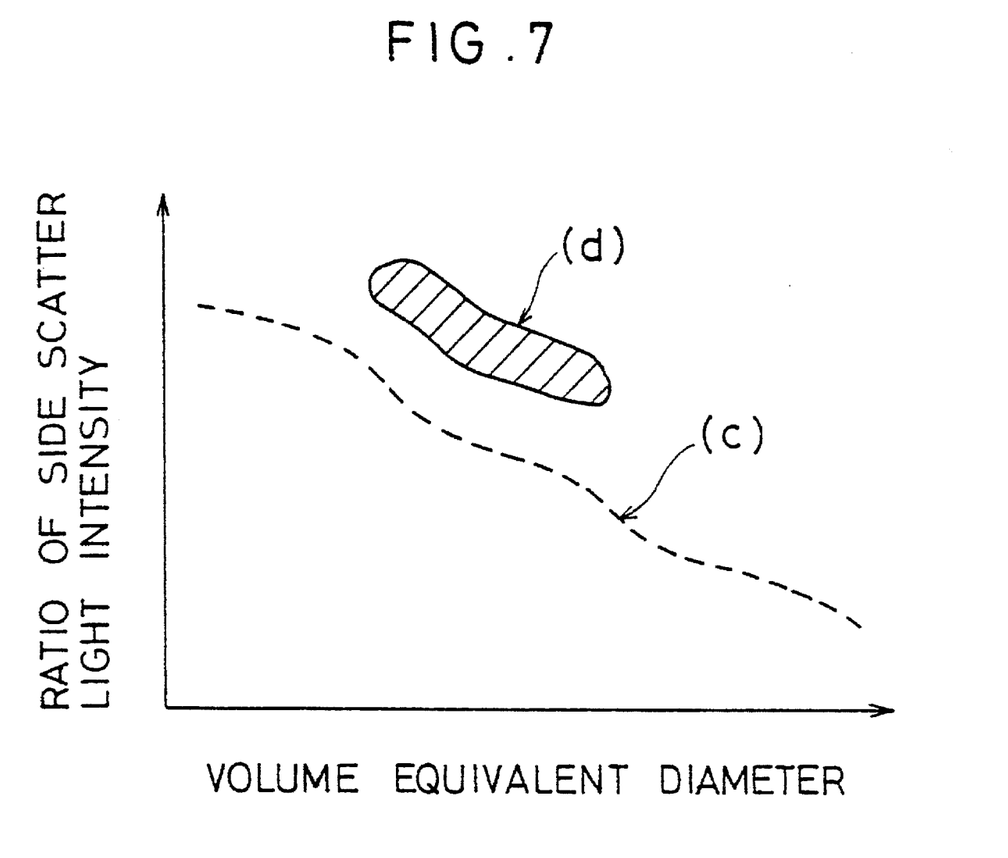
FIG. 7 is a characteristic view showing the relation between the volume-equivalent diameter and an intensity rate of side scatter light.

When the the refractive index of particles to be measured is known and the particles have an approximately round shape, it is possible to know to some extent whether the particles have a smooth surface or to what extent the particles agglutinate to each other by using the relation between the volume-equivalent diameter and the side scatter light intensity or the rate of the side scatter light intensity. FIG. 7 shows such an example. The thick broken line (c) designate a theoretical curve of the intensity rate of the side scatter light determined from the Mie's Scattering Theory by using the particle diameter and the refractive index of particles. The portion (d) shown by the slant lines shows the measurement result of the volume-equivalent diameter and the rate of the side scatter light intensity obtained by actually measuring an actual powder. In this example, the actually measured value (d) of the rate of the side scatter light intensity is higher than the theoretical value (c) of the rate of side scatter light intensity when the particles have a round and smooth surface. When the round particles have the same refractive index, the rate of the side scatter light intensity is higher with respect to particles having a smaller particle diameter. When the surface of the particles is rough, it might, be thought that small particles stick to the surface of large particles. Thus it is possible to say that the rate of the side scatter light intensity becomes larger. Besides, even when the particles have a smooth surface, aggultinated secondary and tertiary particles have a larger rate of the side scatter light intensity than one particle having the same volume-equivalent particle. Consequently, particles measured in this example might have a rough surface. Otherwise, the surface of the particles is oxidized, and the refractive index of the surface is larger than inside of the particle. Otherwise, many aggulinated particles are present therein.

Although it is difficult to quantitatively measure the roughness of the particle surface or the aggultination degree of particles, the index showing the roughness or the aggultination degree can be determined in the following manner. Setting to SRi the mean value of the rate of the side scatter light intensity of ni particles having a volume-equivalent diameter of Vi and the theoretical value thereof to SRti, the difference between the mean value and the theoretical value is normalized with the theoretical value and multiplied by the number of the particles. Thereby a value SNi is determined from the following formula at the outset.

$SNi=((SRi-SRti)/SRti) \times ni.$

Then, with respect to n particles having a volume-equivalent diameter ranging from Va to Vb, the following formula is calculated.

$$SN = \sum_{i=a}^{b} SNi$$

The deviation rate to the theoretical value with respect to n particles can be determined by dividing the SN value by the total number n of particles. When a value obtained by adding 1 to the SN value is set to the surface properties index (SI), the surface properties index (SI) can be obtained in the following manner:

Surface properties index $(SI)=SN/n+1$

When the index is approximate to 1, it designates that the surface is either smooth or aggultinated particles are small in number. Otherwise the same value indicates that the optical properties on the surface portion of particles remains unmodified. The value can be an effective index for monitoring the quality stability in the manufacturing process of particles. Incidentally, in a conventional device of the laser diffraction method for irradiating a large number of particles with a laser beam at the same time, it is difficult to obtain such index.

One of the characteristics of the analyzer of the present invention lies in the accuracy of measurement such that the analyzer can detect more accurately than conventional analyzers that two or more particles pass together through an orifice for detecting a variation in electric resistance. When the orifice has a large diameter and the concentration of particles in the sample liquid is high, a probability is high that two or more particles are arranged in such a manner that the particles adjoin each other. The pulse height of the electric resistance detection signal Sr obtained at that time does not accurately reflect the volume of each particle. In particular, according to this example, the length of the orifice in the orifice portion 1c is prolonged more than normal orifices for more accurately determining the volume of unround particles by the electrozone method. Consequently, a probability is higher that the particles pass through the orifice at the same time.

Figure 3:
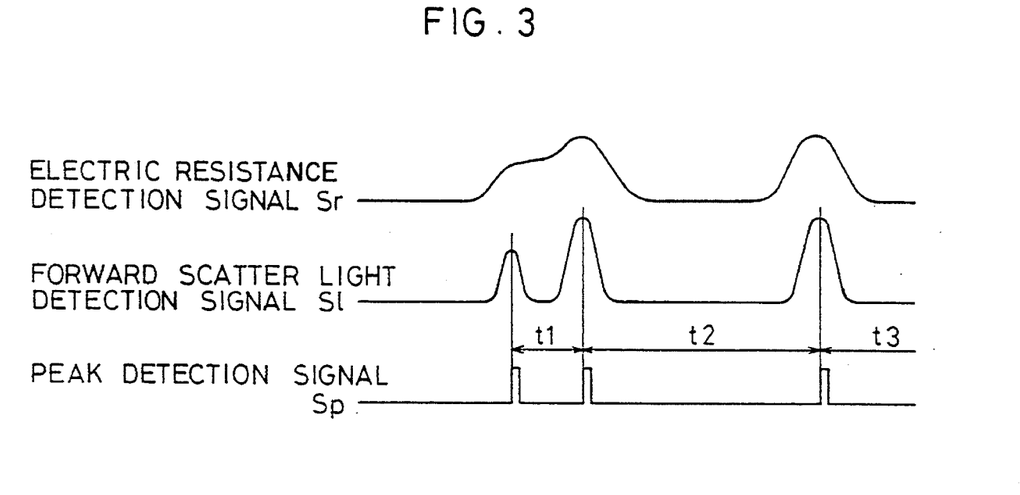
FIG. 3 is a time chart showing signals in an essential portion of the embodiment.

The laser diffraction method can distinguish adjacent particles more accurately than the electrozone method when the measured particle diameter is set to a small level. Consequently, in the laser diffraction method, the scatter light detection signal corresponding to each of the particles is individually detected as a pulse. Thus obtaining information on each interval between the detected pulses allows more accurate judgment than before as to whether two or more adjacent particles pass through the orifice. FIG. 3 shows an example of an electric resistance detection signal Sr and a forward scatter light detection signal S1 when the flow cell 1 is used. FIG. 3 shows a case in which two adjacent particles passes through the orifice, and then one particle pass through the orifice. The electric resistance detection signal Sr is not clearly separated as two detection signals with respect to two adjacent particles. The forward scatter light detection signal S1 is accurately separated into two detection signal pulses. In this invention, along with the scatter light intensity information and electric resistance variation information, information on each interval $ti(i=1,2,3,...)$ between adjacent scatter light detection signals S1 is transmitted to the data analyzer 17 as attribute information with respect to each particle to be stored in a memory. The distance between adjacent particles can be determined from the interval ti and the speed at which the particles pass through the orifice portion 1c. When the distance is shorter than, for example, the length of the orifice portion 1C, the electric resistance variation information is ignored which is obtained with respect to the two particles simply because the pulse height of the electric resistance detection signal Sr does not reflect the accurate volume of particles.

Figure 4:
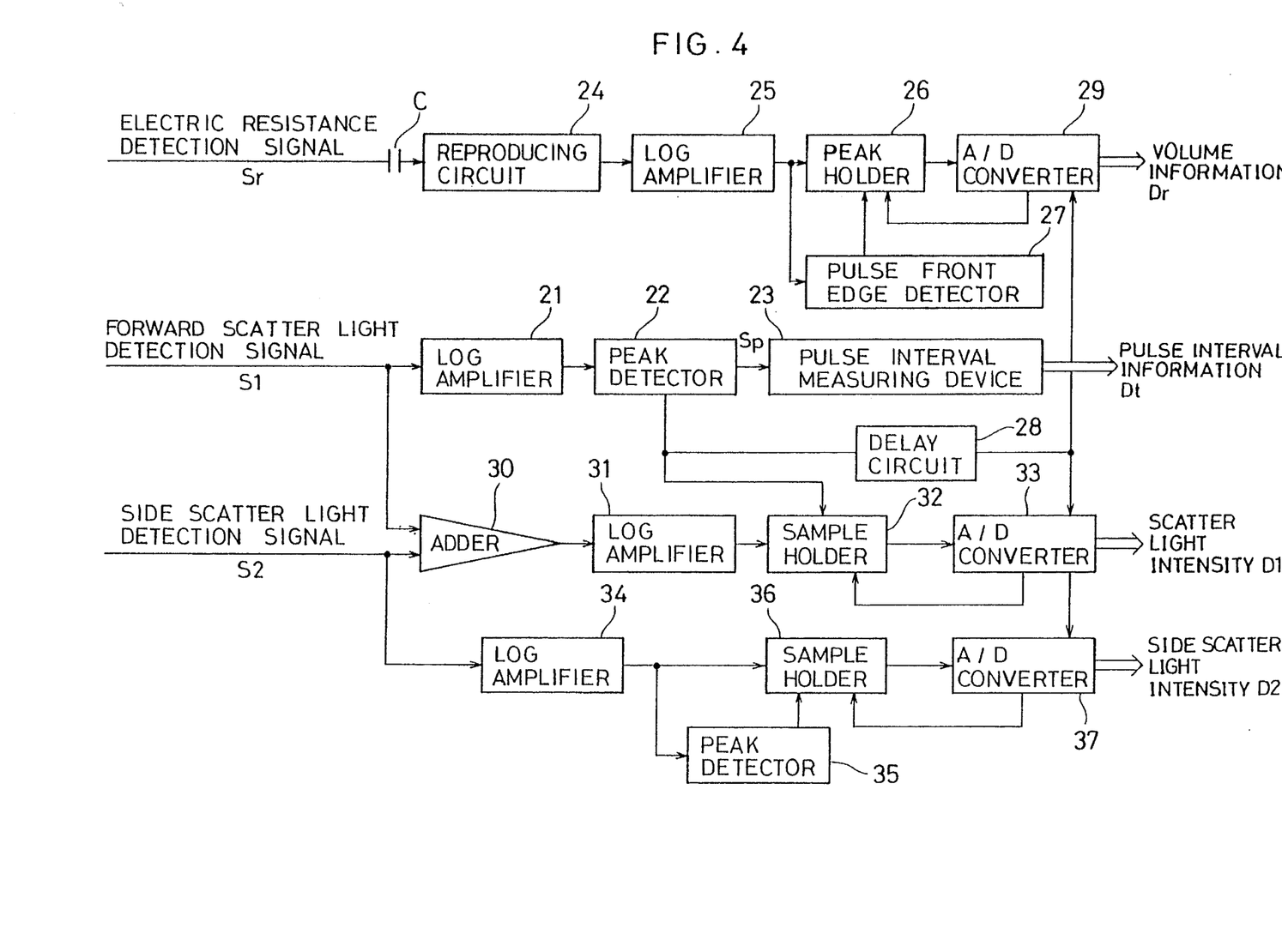
FIG. 4 is a block diagram showing a control circuit in the embodiment.

FIG. 4 shows an example of a structure of the signal processor 16. In this example, since the electric resistance detection signal Sr and the forward and side scatter light detection signals S1 and S2 are obtained almost at the same time, each detection signal is processed based on the detection signal of forward scatter light.

A LOG amplifier 21 non-linearly amplifies the forward scatter light detection signal S1 detected by the photodetector 12. Then the amplified signal S1 is transmitted to a peak detector 22 for detecting a peak of the signal. The LOG amplifier 21 is used, simply because the range of the particle diameter to be measured is wide, and the dynamic range of the obtained detection signal strength is wide. Furthermore, the LOG amplifier 21 is indispensable to obtain the signal intensity as data by using a 10 bit class A/D converter.

The peak detector 22 obtains a peak detection signal Sp corresponding to each particle as shown in FIG. 3. Then the pulse interval device measures each interval ti between pulses of the signal Sp. A high frequency clock signal is input into the pulse interval measuring device 23 (not shown in the drawings). Information Dt on the interval can be obtained with the resolution based on the clock signal. In FIG. 3, for example, the information on interval ti is transmitted to the data analyzer 17 as attribute information with respect to the second particle along with information D1 and D2 on the scatter light intensity of the particles and volume information Dr determined by the variation in the electric resistance.

After a condenser C deprives a DC constituent and a low-frequency fluctuation constituent of the electric resistance detection signal Sr, a reproducing circuit 24 reproduces the electric resistance detection signal and a LOG amplifier 25 non-linearly amplifies the signal Sr. The LOG amplifier 25 transmits the amplified signal to a peak holder 26 and a pulse front edge detector 27. When the pulse front edge detector 27 detects the front edge of the signal Sr, the peak holder 26 is reset. Subsequently, the peak holer 26 holds a peak of the signal Sr. On the other hand, the forward scatter light detection signal S1 is amplified by a LOG ampifier 21 and a peak detection signal Sp (see FIG. 3) of the signal S1 is detected by a peak detector 22. A delay circuit 28 delays the signal Sp for a definite time. An A/D converter 29 initiates the A/D conversion of the signal Sr held in the peak holder 26 when the A/D converter 29 receives the signal Sp. An A/D converter 29 initiates the A/D conversion of the signal Sp.

The undesirable adjustment of the position irradiated with the laser beam on the orifice portion 1C sometimes generates a disagreement in the timing between the peak of the electric resistance detection signal Sr and the peak of the forward scatter light detection signal S1. In order to absorb the shift in the timing, the A/D converter 29 initiates the A/D conversion of the peak of the electric resistance detection signal Sr after the passage of the definite time from the peak of the forward scatter light detection signal S1. Upon the completion of the A/D conversion, the peak holder 26 is reset. The A/D converted data is transferred to the data analyzer 17 as volume information Dr of particles.

After an adder 30 adds the forward scatter light detection signal S1 to the side scatter light detection signal S2, a LOG amplifier 31 transfers the added signals to a non-linear amplifier 31. A sample holder 32 holds an output of the amplifier 31, when the peak detector 22 detects the peak of the forward scatter light detection signal S1. Then after the passage of a definite time, an A/D converter 33 initiates the A/D conversion of the signal held in the sample holder 32 to determine information D1 on the scatter light intensity which is obtained by adding the forward scatter light intensity to the side scattered light intensity. Upon completion of the A/D conversion, the sample holder 32 is relieved of the held state.

The signal processor shown in FIG. 4, also obtains individual information on the side scatter light intensity. After a LOG amplifier 34 non-linearly amplifies the side scatter light detection signal S2, the LOG amplifier 34 transfers the signal S2 to a peak detector 35 and a sample holder 36. When the peak detector 35 detects a peak of the side scattered light detection signal S2, the sample holder 36 holds the signal S2. Then the A/D converter 37 A/D converts the held signal to determine information D2 on the side scattered light intensity.

The signal processor 16 transfers the obtained information to the data analyzer 17 where a judgment is passed as to whether particles have passed through the orifice at the same time from the aforementioned interval information ti obtained with respect to individual particles. Then the data analyzer 17 selects only information on the particles which has been judged to avoid the simultaneous passage through the orifice thereby determining a volume-equivalent diameter from the information on volume, and at the same time calculates a scatter light intensity-equivalent diameter from the scatter light intensity. Processing such items of data allows displaying of the particle size distribution and two-dimensional distribution as shown in FIGS. 5, 6 and 7. As described above, different items of data are also processed to calculate the rate of the side scatter light intensity, the refractive index, and the index of roundness. The particle concentration in the sample liquid is determined by such factors as measuring time, the amount of analyzed sample, and the number of information (data) items obtained in the analysis. The number of information items obtained refers to the number of scatter light signal pulses obtained in the measured period. They require virtually no simultaneous passage correction.

In addition, the above pulse interval information is used to check whether the sheathed flow has been stable in the measurement period. For example, it is possible to check whether the orifice is clogged with large particles or agglutinated particles in the midst of measurement by calculating each mean value of interval information ti per 100 particles or the cumulative value thereof. In addition, time is notified which is needed from the initiation of the transportation of the sample liquid to the flow cell 1 until the stablization of the sheathed flow.

Figure 8:
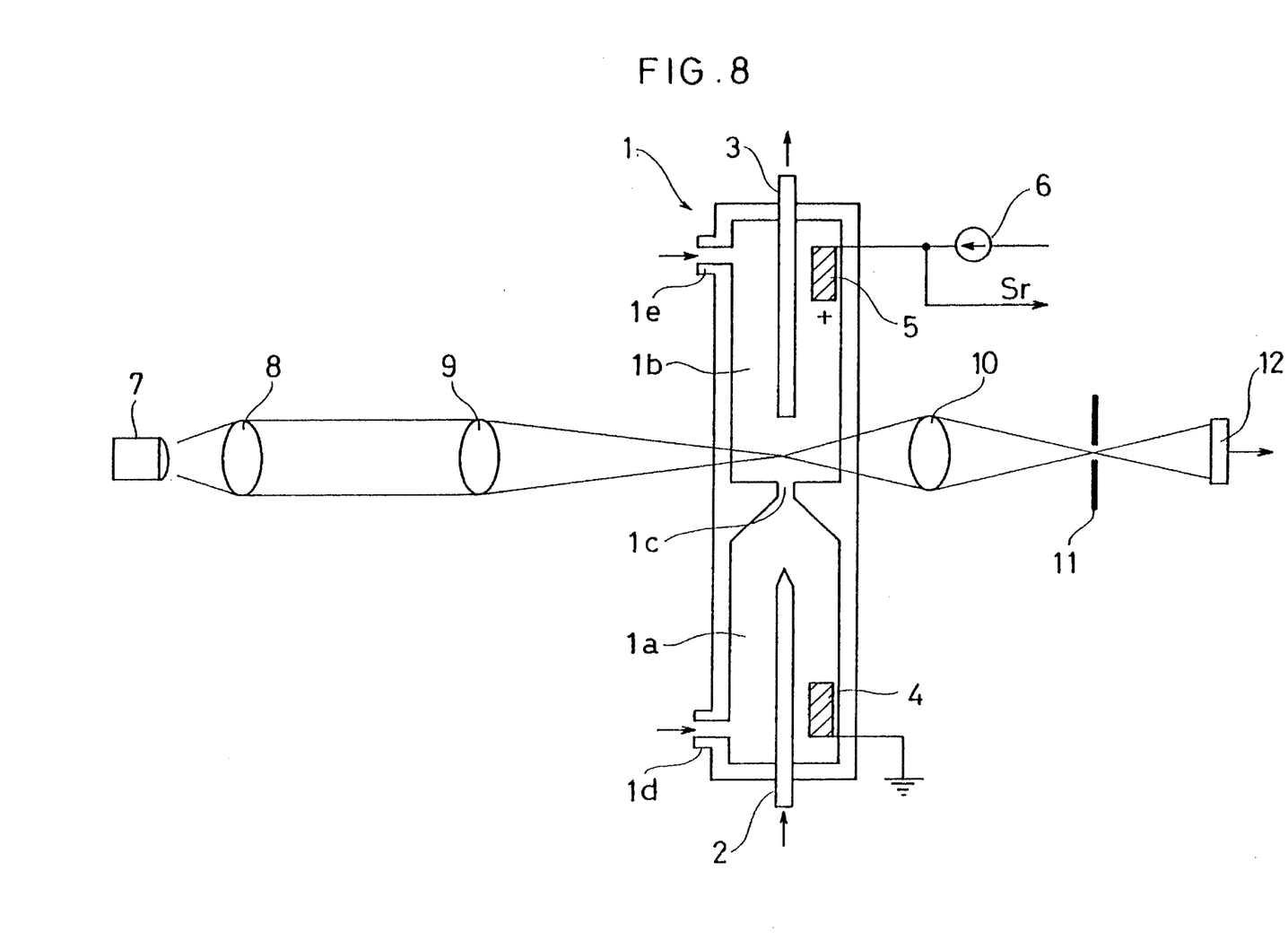
FIG. 8 is a side view illustrating a structure of a modification of the embodiment of FIG. 1.

Then, FIG. 8 is a partially modified example of embodiment 1 shown in FIG. 1.

In FIG. 8, the particle analyzer irradiates particles with a laser beam immediately after the particles pass through the orifice of the orifice portion 1c. Scatter light is detected after the change in the electric resistance is detected. Other aspects of the structure is the same as the embodiment shown in FIG. 1. In this particular embodiment, the orifice has a smaller diameter than the counterpart in the embodiment shown in FIG. 1 so that volume information can be obtained with respect to even small particles. This is because in the embodiment shown in FIG. 1 irradiation of the orifice portion 1c with the laser beam is likely to generate stray light with the presence of the inside wall of the orifice with the result that a high process precision is demanded for the formation of the orifice and the diameter of the orifice cannot be made small so much.

The present invention has the following advantages.

1. The present invention enables measuring even small particles by adding a electric resistance detection system with an detecting orifice to a scatter light detection system and also enables enlarging the range of the diameter of particles that can be measured.

2. With respect to particles whose electric resistance variation amount (volume information) and scatter light intensity information can be obtained, 1) the present invention enables obtaining various indexes such as refractive index of particles, roundness of particles, and smoothness of particle surface as well as volume-equivalent diameter; and 2) the present invention allows the indexes described in 1) to be effectively used for monitoring the stability in the quality of products in the manufacturing of particles.

3) With respect to small particles with which only scatter light information can be obtained, the present invention enables inferring the refractive index of the particles from the relations between the volume-equivalent diameter and the scatter light intensity obtained with respect to a different group of particles larger than the particle to be measured. The present invention also allows obtaining more accurate particle diameter (scatter light intensity-equivalent diameter) even when the refractive index and the surface state are not made clear.

3. The present invention incorporates into data even intervals between scatter light signal pulses obtained by the scatter light detection system, thus making it possible to determine from the interval information whether or not the particles pass through the orifice at the same time. The present invention provides more accurate particle size distribution information than before by selecting only information on particles which are judged not to be passing through the orifice at the same time.

4. The aforementioned interval information makes it possible to check whether the sheath flow has been stable in the measurement period, or whether the orifice is clogged which is used for detecting, for example, electric resistance variation.

What is claimed is:

1. A particle analyzer comprising:
   a flow cell for enclosing an electrolyte containing particles in a sheathed flow, the flow cell including a first and a second cells which are interconnected through an orifice, the sheathed flow flowing through the orifice from the first cell to the second cell;
   a first and second electrodes provided in the first and the second cells, respectively;
   voltage application means for applying voltage between the first and second electrodes;
   resistance detection means for detecting a variation of electric resistance between the first and second electrodes when the particle passes through the orifice to output the detected variation as a resistance detection signal;
   first diameter calculation means for calculating each diameter of the particles based on the detected variation of electric resistance;
   light source means for emitting a light beam to the particles enclosed in the sheathed flow;
   light detection means for detecting each intensity of scatter light of the particles irradiated with the light beam to output the detected intensity as a scatter light detection signal;
   refractive index calculation means for calculating a refractive index of the particle based on the resistance detection signal and the scatter light detection signal; and
   second diameter calculation means for calculating each diameter of the particles based on the calculated refractive index and the scatter light detection signal.

2. A particle analyzer according to claim 1 further comprising measuring means for measuring intervals between the scatter light detection signals obtained when a plurality of particles serially flow in the sheath flow, and particle size distribution calculation means for calculating a particle size distribution based on the calculated diameters of the particles except the particles of which scatter light detection signals have intervals shorter than a predetermined time.

3. A particle analyzer according to claim 2 further comprising calculation means for calculating an mean value or a cumulative value of the intervals measured with respect to a predetermined number of particles to monitor a clogging state of the orifice or a stability of the sheathed flow.

4. A particle analyzer according to claim 1 wherein the light detection means comprises first light detection means for detecting an intensity of forward scatter light of The particle to output the detected intensity as a forward scatter light detection signal, second light detection means for detecting an intensity of side scatter light of the particle to output the detected intensity as a side scatter light detection signal, and adding means for adding the forward scatter light detection signal to the side scatter light detection signal to output the added signals as the scatter light detection signal.

5. A particle analyzer according to claim 4 further comprising index calculation means for calculating an index of roundness or agglutination rate of the particle from a deviation of the intensity of side scatter light obtained with respect to a plurality of particles which are the same in magnitude of the resistance detection signal.

6. A particle analyzer according to claim 4 further comprising ratio calculation means for calculating a ratio of the forward or side scatter light intensity to the scatter light intensity, and index calculation means for calculating an index of roundness or agglutination rate of the particle from a deviation of the ratio calculated with respect to a plurality of particles which are the same in magnitude of the resistance detection signal.

7. A particle analyzer according to claim 4 further comprising ratio calculation means for calculating a ratio of the forward or side scatter light intensity to the scatter light intensity with respect to a plurality of particles having a nearly spherical shape and a known refractive index, and an index calculating means for calculating an index of surface smoothness, surface optical characteristics, or agglutination rate of the particle.

* * * * *